(12) United States Patent
West et al.

(10) Patent No.: US 8,318,037 B2
(45) Date of Patent: Nov. 27, 2012

(54) ORGANOSILICON GLYCOL-BASED ELECTROLYTES WITH A HYDROXY TERMINUS

(75) Inventors: Robert C. West, Madison, WI (US); Jose A. Pena Hueso, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 406 days.

(21) Appl. No.: 12/770,813

(22) Filed: Apr. 30, 2010

(65) Prior Publication Data

US 2011/0266490 A1  Nov. 3, 2011

(51) Int. Cl.
*H01G 9/035* (2006.01)

(52) U.S. Cl. ....... 252/62.2; 361/503; 361/504; 361/506; 429/347; 429/341

(58) Field of Classification Search .................. 252/62.2; 361/503, 506, 504; 429/347, 341
See application file for complete search history.

(56) References Cited

U.S. PATENT DOCUMENTS

| | | | |
|---|---|---|---|
| 6,058,006 A | 5/2000 | Yoshioka et al. | |
| 2003/0124432 A1 | 7/2003 | Miura et al. | |
| 2005/0106470 A1 * | 5/2005 | Yoon et al. | 429/324 |
| 2007/0065728 A1 | 3/2007 | Zhang et al. | |
| 2007/0076349 A1 | 4/2007 | Dementiev et al. | |
| 2010/0053847 A1 | 3/2010 | Tani et al. | |

FOREIGN PATENT DOCUMENTS

| | | |
|---|---|---|
| JP | 9025282 | 1/1997 |
| JP | 2007123097 | 5/2007 |

OTHER PUBLICATIONS

L. Zhang et al., Highly Conductive Trimethylsilyl Oligo(ethylene oxide) Electrolytes for Energy Storage Applications, 18 J. Mater. Chem. 3713-3717 (2008).

U. Yoon et al., Efficient and Regioselective Photocyclization Reactions of N-[(ω-Trimethylsilylmethoxy)Polyoxyalkyl]Phthalimides to Azacrown Ethers, 41 Heterocycles 2665-2682 (1995).

12 pages of an ISR from corresponding PCT application PCT/US2011/030415 dated Jun. 29, 2011.

* cited by examiner

*Primary Examiner* — Carol M Koslow

(74) *Attorney, Agent, or Firm* — Quarles & Brady LLP

(57) ABSTRACT

Disclosed are hydroxy terminated alkylsilane ethers with oligoethylene oxide substituents. They are suitable for use as electrolyte solvents and particularly well suited for use with aqueous environment electrolytic capacitors. Methods for synthesizing these compounds are also disclosed.

9 Claims, No Drawings

ORGANOSILICON GLYCOL-BASED ELECTROLYTES WITH A HYDROXY TERMINUS

FEDERALLY SPONSORED RESEARCH/DEVELOPMENT

This invention was made with government support under 0724469 awarded by the National Science Foundation. The government has certain rights in the invention.

CROSS-REFERENCE TO RELATED APPLICATIONS

Not applicable.

BACKGROUND OF THE INVENTION

The present invention relates to ionic electrolytes useful in connection with electrolytic capacitors and certain other energy storage devices. More particularly it relates to hydroxy terminated organosilicon electrolytes that are particularly useful in an aqueous electrolytic capacitor environment.

Over the past decade our laboratory has been developing organosilicon based electrolytes for energy storage applications. Various of these organ silicon compounds have low vapor pressure, high flash point, and withstand high operating voltages.

For example, we previously reported the synthesis of some alkyl terminated trimethylsilyl oligoethylene glycol ethers in L. Zhang et al., Highly Conductive Trimethylsilyl Oligo(ethylene oxide) Electrolytes For Energy Storage Applications, 18 J. Mater. Chem. 3713-3717 (2008). These materials had high ionic conductivity, good electrochemical stability, and good cycling performance when used as electrolyte solvents in lithium-ion cells. However, they were susceptible to being hydrolyzed under some conditions.

We also reported in U.S. patent application publication 2007/0065728 the concept of placing an alkyl spacer in such alkyl terminated compounds between the trimethylsilyl group and the remainder of the molecule. This helped the molecule resist hydrolysis. However, the compounds still did not achieve desired performance in certain environments.

One reason is that a variety of electrolytic capacitors use water to repair aluminum defects. See generally descriptions of electrolytic capacitors in U.S. Pat. No. 6,058,006. Conventional aluminum electrolytic capacitors sometimes use an electrolyte mix of gamma-butyrolactone, diethylene glycol, triethylammonium azelaate, and water. To achieve the advantages of our alkyl terminated organosilicon compounds with this type of capacitor there were attempts to replace the gamma-butyrolactone and diethylene glycol with them. However, alkyl terminated organosilicon electrolytes typically had performance issues in this environment.

In U. Yoon et al., Efficient And Regioselective Photocyclization Reactions Of N—[(ω-Trimethylsilylmethoxy)Polyoxalkyl]Phthalimides To Azacrown Ethers, 41 Heterocycles 2665-2682 (1995) the authors reported the synthesis of Me$_3$Si—CH$_2$OCH$_2$CH$_2$OCH$_2$CH$_2$OCH$_2$CH$_2$—OH, Me$_3$Si—CH$_2$OCH$_2$CH$_2$OCH$_2$CH$_2$—OH and Me$_3$Si—CH$_2$OCH$_2$CH$_2$OCH$_2$CH$_2$OCH$_2$CH$_2$—OH (and various related compounds) as intermediates in the production of azacrown ethers. Apart from the fact that their syntheses required use of relatively expensive Me$_3$Si—CH$_2$I, there was no suggestion in their article to use these intermediates as electrolytes.

There is therefore a need for additional improvements with respect to organosilicon electrolytes for energy storage devices, particularly improvements relating to compatibility with water environments.

SUMMARY OF THE INVENTION

In one aspect the invention provides an electrolyte comprising:
a salt; and
at least one compound having the following formula:

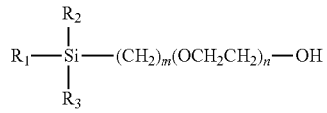

In this compound $R_1$, $R_2$ and $R_3$ are the same or different, and each is selected from the group consisting of alkyl moieties of less than five carbons. Most preferably each of $R_1$, $R_2$ and $R_3$ is $CH_3$. In any event, both m and n are less than 10, with m and n both most preferably lower than 5, and even more preferably with n equal to 2, 3 or 4.

One preferred salt for use with such electrolytic capacitors is triethylammonium azelaate, e.g. at less than 2% of the electrolyte. However, alternatively other conventional salts useful with such energy storage devices can be included. See e.g. U.S. patent application publication 2010/0053847 regarding varied salts useful with such capacitors. Various lithium based salts are also known to be compatible with a variety of organosilicon electrolytes.

Electrolytes can be created with mixtures of multiple such compounds. Alternatively, one of these compounds can be used with other materials (e.g. ethylene glycols; ditrimethyl silane terminated compounds).

The electrolytes of the present invention are particularly suitable for use in environments where they will be exposed to/mixed with water. For example, aluminum electrolytic capacitors typically add a few percent of water to their electrolytic solution to help repair the aluminum material.

In another aspect the invention provides an energy storage device (e.g. an electrolytic capacitor) which has such an electrolyte.

In yet another form the invention provides methods of producing hydroxy terminated organosilicon compounds having the following formula:

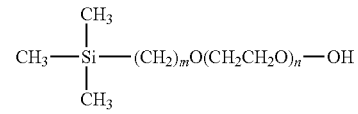

In these compounds m and n are both less than 10, preferably both less than 5. To produce them one reacts HO(CH$_2$CH$_2$O)$_r$—OH with sodium cation, and then reacts the resultant with Me$_3$Si(CH$_2$)$_q$Cl and iodide anion. Here, q and r are both less than 10.

It will be appreciated that the present invention provides electrolytes that are highly useful in energy storage devices where the electrolyte contains or is exposed to water (e.g. especially in aluminum electrolytic capacitors). These electrolytes resist hydrolysis, can be used at relatively high voltages, and have reduced flammability concerns. Note that as n increases the flashpoint of these compounds also increases.

The present invention also provides improved methods of synthesizing such compounds. In this regard, Me₃Si(CH₂)I, a starting material used in prior art syntheses, is undesirably expensive. Its use is avoided by replacing that compound with Me₃Si(CH₂)Cl and catalytic amounts of iodide anion, and adjusting concentrations and reaction conditions to minimize undesired byproducts.

The above and still other advantages of the present invention will be apparent from the description that follows. It should be appreciated, however, that the following description is merely of the preferred embodiments. The claims should therefore be looked to in order to understand the more comprehensive nature of the claimed invention.

DESCRIPTION OF THE PREFERRED EMBODIMENTS

We first describe improved syntheses for producing hydroxy terminated organosilicon compounds having the following formula:

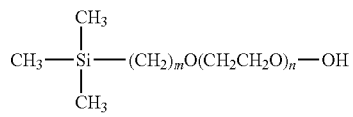

EXAMPLE 1

Mixture of 75% Me₃Si—CH₂OCH₂CH₂OCH₂CH₂—OH with about 20% HO—CH₂CH₂OCH₂CH₂OH, and about 5% Me₃Si—CH₂OCH₂CH₂OCH₂CH₂OCH₂CH₂—SiMe₃

700 mL of diethyleneglycol are mixed with 38 g of powdered NaOH and the mixture is stirred under vacuum at 80° C. for 4 hours to eliminate most of the water produced in the reaction. After this time the NaOH was essentially completely dissolved and the liquid no longer boiling.

The temperature was then lowered to 70° C. and 21 g of NaI was added. Note that increasing the NaI levels above 20% molar equivalent would greatly increase byproducts and cost, and we selected our sodium iodide level lower accordingly.

Vacuum is no longer needed at this point and the mixture is stirred until all NaI dissolves (about 30 minutes). Then 116 g of chloromethyltrimethylsilane are added, and the mixture is stirred for 3 hours at 70° C. and 1 hour at 80° C. After this 200 mL of water are added to the mixture and it is extracted with hexane (4×300 mL), the hexane is evaporated in rotavapor and the compound distilled. This lead to an initial yield of 160 g of the 75/20/5 mixture. Interestingly, even this intermediate mixture turned out to have significant utility as an electrolyte.

EXAMPLE 2

Me₃Si—CH₂OCH₂CH₂OCH₂CH₂—OH

In order to obtain a higher purity of the Example 2 product, the Example 1 mixture was dissolved in 500 mL of water plus 1.5 L of methanol and the nonpolar impurities extracted with hexane (2×75 mL). The solvent was then evaporated and the remaining compound dissolved in 1.5 L of hexane and extracted with water (2×100 mL). The solvent was then evaporated. Yield 115 mL, 98% pure.

EXAMPLE 3

Me₃Si—CH₂OCH₂CH₂OCH₂CH₂OCH₂CH₂—OH 700 mL of triethyleneglycol are mixed with 45 g of powdered NaOH and the mixture is stirred under vacuum at 90° C. for 3 hours to eliminate most of the water produced in the reaction. After this time the NaOH should be completely dissolved and the liquid no longer boiling.

The temperature is then lowered to 70° C. and 24 g of NaI are added. Vacuum is no longer needed and the mixture is stirred until all NaI dissolves (about 30 minutes). Then 135 g of chloromethyltrimethylsilane are added and the mixture is stirred for 3 hours at 70° C. and 1 hour at 80° C. After this 70 mL of water are added to the mixture and it is extracted with hexane (3×300 mL).

Half of the solvent is evaporated in rotavapor and 50 mL of water are added to extract polar impurities. After that the remaining hexane is evaporated and the Example 3 compound distilled. Yield 180 g, 95% pure.

EXAMPLE 4

Me₃Si—CH₂OCH₂CH₂OCH₂CH₂OCH₂CH₂OCH₂CH₂—OH 400 mL of tetraethyleneglycol are mixed with 18.5 g of powdered NaOH and the mixture is stirred under vacuum at 90° C. for 3 hours to eliminate most of the water produced in the reaction. After this time the NaOH should be completely dissolved and the liquid no longer boiling. The temperature is lowered to 70° C. and 10.5 g of NaI are added.

Vacuum is no longer needed and the mixture is stirred until all NaI dissolves (about 30 minutes). Then 56.4 g of chloromethyltrimethylsilane are added and the mixture is stirred for 3 hours at 70° C. and 1 hour at 80° C. After this 50 mL of water are added to the mixture and it is extracted with hexane (3×200 mL). The solvent is evaporated in rotavapor and the compound distilled. After this 50 mL of water are added and 10 mL of hexane to extract nonpolar impurities. The water is evaporated in the rotavapor to give the compound. Yield 80 g.

Once we have a desired electrolyte (or electrolyte mixture) one can add a conventional electrolyte salt, preferably at less than 2%, and use that material in an energy storage device such as an aluminum electrolytic capacitor.

In addition to compound(s) of the present invention the electrolytes can also have mixed therein various polyethylene glycol compounds and/or a ditrimethyl silane terminated electrolyte.

Various electrolytes of the present invention have been tested in aluminum electrolytic capacitors. They have been found to resist hydrolysis and to be otherwise compatible with an aqueous environment, while still achieving other desirable properties expected from their alkyl terminated counterparts.

While various embodiments of the present invention have been described above, the present invention is not limited to just these disclosed examples. There are other modifications that are meant to be within the scope of the invention and claims. For example, m and n could have larger numbers than the preferred embodiments exemplify.

Thus, the claims should be looked to in order to judge the full scope of the invention.

INDUSTRIAL APPLICABILITY

The present invention provides improved electrolytes, particularly electrolytes suitable for use in aqueous electrolytic capacitor environments. Improved methods for making them are also described.

We claim:
1. An electrolyte comprising:
a salt; and
at least one compound having the following formula:

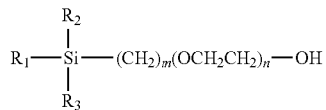

wherein $R_1$, $R_2$ and $R_3$ are the same or different, and each is selected from the group consisting of alkyl moieties of less than five carbons; and
wherein m and n are both not zero and both are less than 10.

2. The electrolyte of claim 1 wherein each of $R_1$, $R_2$ and $R_3$ is $CH_3$.
3. The electrolyte of claim 1, wherein m is lower than 5.
4. The electrolyte of claim 1, wherein n is 2 or 3 or 4.
5. The electrolyte of claim 1, further comprising water.
6. The electrolyte of claim 1, further comprising an ethylene glycol.
7. The electrolyte of claim 1, further comprising a ditrimethyl silane terminated electrolyte.
8. An energy storage device comprising the electrolyte of claim 1.
9. The energy storage device of claim 8, wherein the energy storage device is an aluminum electrolytic capacitor.

* * * * *